US00PP25152P3

(12) United States Plant Patent
Clark et al.

(10) Patent No.: US PP25,152 P3
(45) Date of Patent: Dec. 9, 2014

(54) GRAPE PLANT NAMED 'A-1710'

(50) Latin Name: ***Vitis labrusca* L.×*Vitis vinifera* L.**
Varietal Denomination: A-1710

(75) Inventors: John R. Clark, Fayetteville, AR (US); James N. Moore, Fayetteville, AR (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 640 days.

(21) Appl. No.: 13/068,760

(22) Filed: May 19, 2011

(65) Prior Publication Data

US 2012/0297511 P1 Nov. 22, 2012

(51) Int. Cl.
*A01H 5/00* (2006.01)
*A01H 5/08* (2006.01)

(52) U.S. Cl.
CPC ..... *A01H 5/0812* (2013.01)
USPC ..... Plt./205; Plt./206

(58) Field of Classification Search
CPC ..... A01H 5/0812
USPC ..... Plt./205, 206
See application file for complete search history.

*Primary Examiner* — June Hwu
*Assistant Examiner* — Louanne Krawczewicz Myer
(74) *Attorney, Agent, or Firm* — Andrus Intellectual Property Law, LLP

(57) ABSTRACT

Description and specifications of a new and distinct grapevine cultivar which originated from a hand-pollinated cross of Moored (non-patented)×NY 45791 (non-patented, non-released breeding genotype). This new grapevine cultivar can be distinguished by its seedless, pink berries of distinct *V. labrusca*-like flavor, small compact clusters, distinctly lobed leaves, medium vigor, and healthy plant.

3 Drawing Sheets

Latin name: *Vitis labrusca* L.×*Vitis vinifera* L.
Varietal denomination: 'A-1710'.

BACKGROUND

The new and distinct cultivar of grape named 'A-1710' is described herein. The new cultivar originated from a hand-pollinated cross of Moored and NY 45791 made in 1976. The seedlings fruited in the summer of 1979 in a vineyard near Clarksville, Ark. and one was selected for its seedless, pink berries with good flavor. The fruit grows in compact clusters, the vines have medium vigor and the plants are healthy.

SUMMARY OF THE INVENTION

The new and distinct cultivar of grapevine originated from a and-pollinated cross of Moored (non-patented; female)× NY 45791 (non-patented, non-released breeding genotype; male) made in 1976 near Clarksville, Ark. The instant cultivar is a hybrid of *Vitis labrusca* L. and *Vitis vinifera* L. The seeds resulting from this controlled hybridization were germinated in a greenhouse during the winter of 1976-77. Resulting seedlings were planted in the spring of 1977 in a vineyard near Clarksville, Ark. The seedlings fruited in the summer of 1979 and one, designated Arkansas Selection 1710, was selected for its seedless, pink berries of distinct *V. labrusca*-like flavor, small compact clusters, distinctly lobed leaves, medium vigor, and healthy plant.

During late 1979 and early 1980, the original plant selection was propagated asexually at the above-noted location, by rooting hardwood cuttings and a test planting of three vines was established. In all propagations hardwood cuttings were used and the instant cultivar rooted readily from hardwood cuttings. All propagules (resulting plants) of the instant cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have medium vigor, with a procumbent growth habit characteristic of *V. labrusca*. It has produced well as own-rooted plants in all testing and has not been evaluated on any rootstocks. Hardiness of the vines have been very good, with no winter injury to the vines to 5° F. in the most severe winters at the Arkansas test site.

The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). Fungal diseases can be controlled by the use of available fungicides.

The new cultivar ripens its fruit in the early season, average July 15. The fruit is pink in color at early maturity. It is evenly colored within the cluster. The fruit shape is round. Fruit skins are medium-thick and do not adhere to the flesh (has a slip-skin texture). The berries are medium-small (ca. 3.1 g). The flavor is very pronounced and distinctive, and of a *V. labrusca* character. Solids concentration of the juice at fruit maturity averages 22% with medium acidity. The fruit is of the stenospermocarpic type of seedlessness and can contain 1-2 small, soft vestigial seed traces that are not noticeable when eaten. Fruit clusters, borne usually two to three per shoot, are small, compact and tightly filled with an average weight of 150 g. The fruit clusters are considered limited in size for commercial markets and the variety is intended for home garden planting.

The new cultivar has been named the 'A-1710' cultivar.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR

Figure 1:
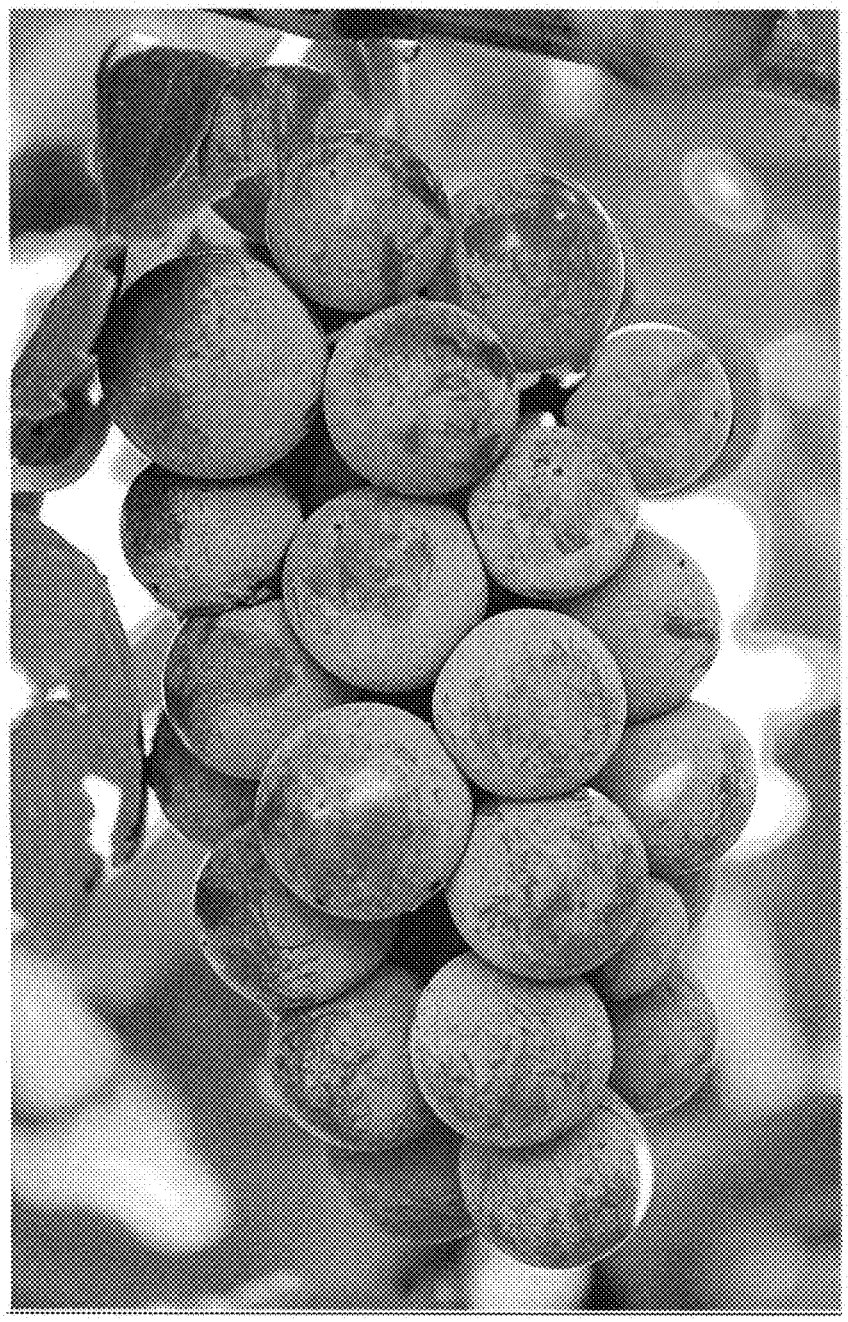
FIG. 1 is a photograph showing typical specimens of the fruit.
Figure 2:
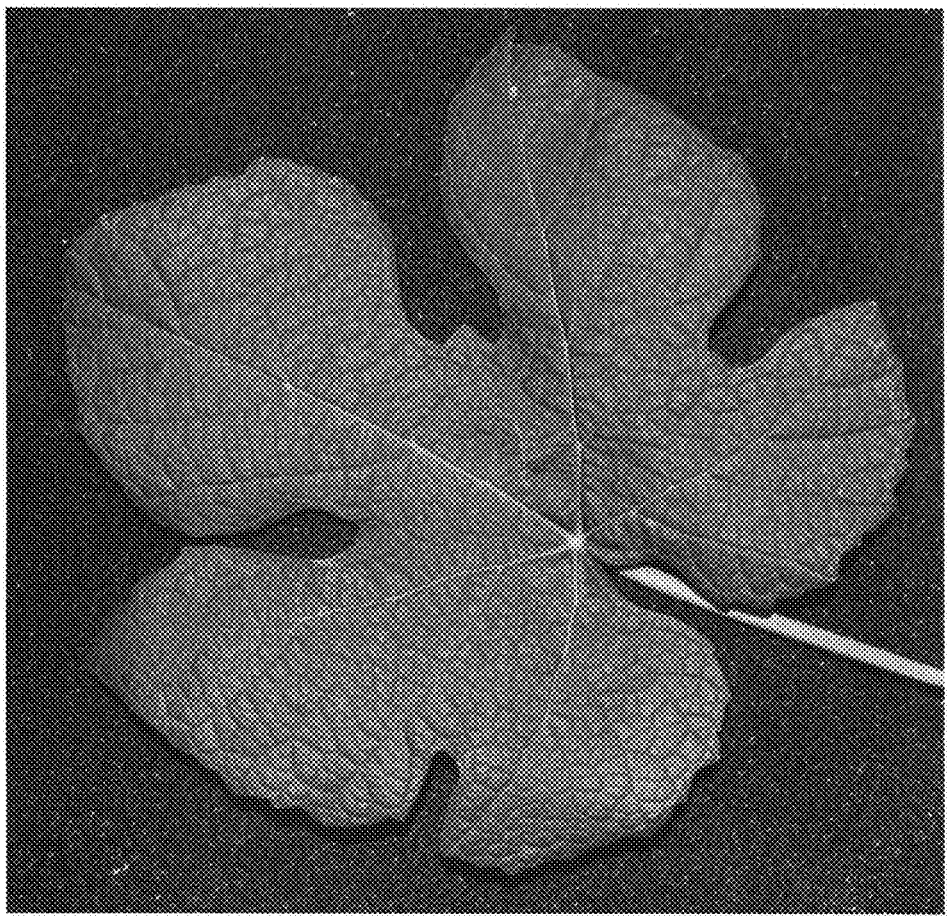
FIG. 2 is a photograph showing the leaf adaxial view.
Figure 3:
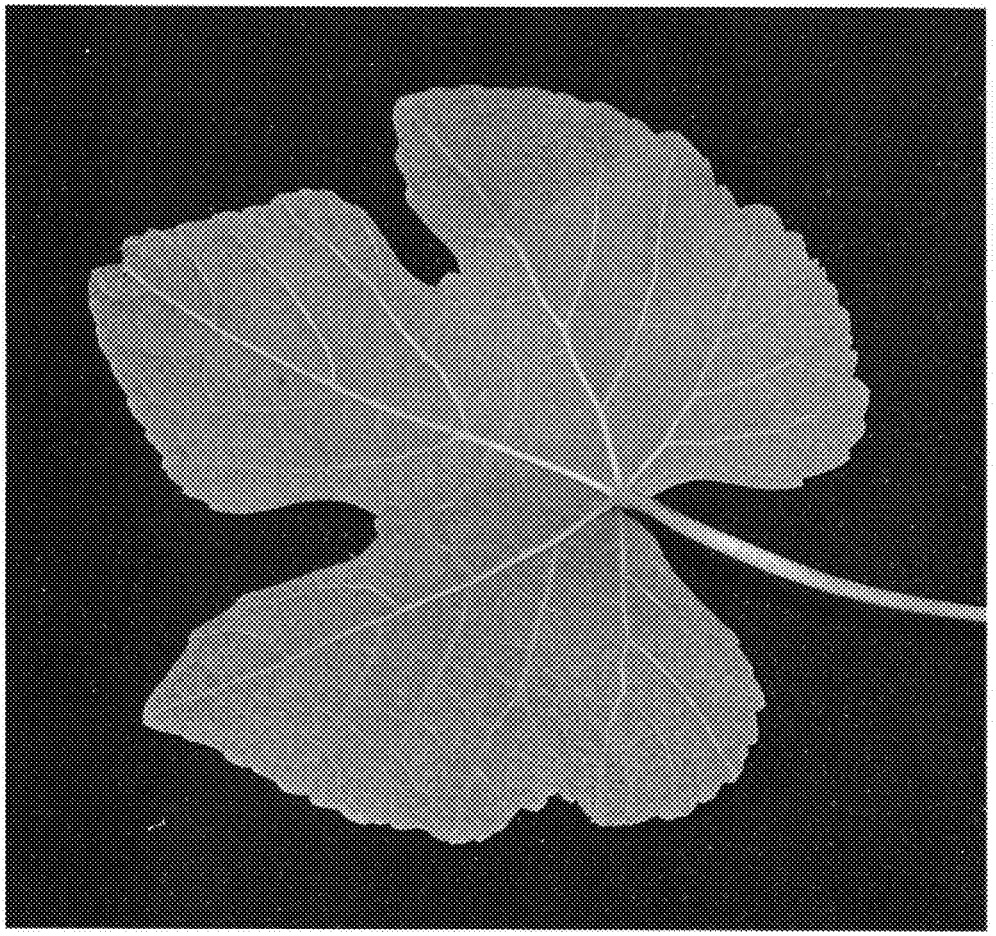
FIG. 3 is a photograph showing the leaf abaxial view.

'A-1710' differs from its female parent Moored in that it has smaller clusters, more pink-like berry color compared to red color for Moored, and is seedless. A-1710 has distinctly lobed leaves unlike either parent. A-1710 differs from it male parent NY 45791 as this parent is blue/black in fruit color, has much larger clusters, and the parent has more loosely filled clusters. A-1710 differs from a comparable *Vitis labrusca* cultivar Mars (U.S. Plant Pat. No. 5,680) in that A-1710 has much smaller clusters than Mars, pink fruit rather than black as Mars does, smaller berries than Mars, ripens approx. 3 weeks earlier than Mars, and has deeply lobed leaves while Mars leaves are only minimally lobed. Additionally, Mars is higher in vigor than A-1710. The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. The data collection was from vines that were 15 years old.

Vine:

*Size*.—Medium.

*Growth*.—Moderately vigorous.

*Density of foliage*.—Medium.

*Productivity*.—Moderately productive.

*Rootstock*.—None; vines tested were own-rooted vines.

*Cold hardiness*.—Hardy to 5° C. (−15° C.); possibly more hardy as this was the coldest temperature experienced at the test site.

Shoots (current-season canes):

*Color of shoots on the side exposed to direct sunlight*.—Greyed-Purple Group (183A).

*Color on the side shaded from the sun*.—Yellow-Green Group (146C).

*Anthocyanin*.—Present on the shoot sides exposed to direct sunlight.

*Shoot*.—Attitude is procumbent.

Canes (mature measured in winter):

*Color of mature cane*.—Base mostly Greyed-Orange Group (165A) and some 177B; midpoint mostly Greyed Orange Group (165B) and some 177B; terminal Greyed-Orange Group (165B) and some 177B; anthocyanin observed on mature canes at base, midpoint, and terminal.

*Surface texture of mature cane*.—Slightly uneven, giving it a rough texture, but the bark itself is actually smooth.

*Length*.—Average 265 cm with range of 126 to 485 cm.

*Diameter of mature cane*.—Base 0.83 cm, midpoint 0.7 cm, terminal 0.3 cm.

*Internode length*.—Base 3.9 cm, midpoint 10.6 cm, terminal 8.2 cm.

*Lenticels*.—Present on mature canes at medium density and small (less than 0.5 mm in diameter).

*Canes*.—Mature to tips in the fall.

Trunk:

*Shape*.—Slender.

*Trunk straps*.—Long, split.

*Trunk diameter at* 30 *cm above the ground*.—36.7 mm.

*Surface texture*.—Shaggy.

*Inner bark color*.—Greyed-Orange Group 177C.

*Outer bark color*.—Greyed-Green Group 197C.

Foliage:

*Leaves*.—Leaves simple and alternate; shape palmate; number of lobes 5; petiole sinus shape half open; venation palmate-pinnate; margin serrated with shape of teeth convex and teeth short in size. The surface has a rugose texture on the abaxial side, a smooth texture on the adaxial side. Mature leaves have heavy blistering.

*Size and texture of mature leaves*.—Length — 14.5 cm. Width — 14.7 cm. Thickness — 0.3 mm.

*Color of mature leaves*.—Base abaxial-Yellow-Green Group (148B); base adaxial — Green Group (139A); midpoint abaxial — Yellow-Green Group (148B); midpoint adaxial — Green Group (137A); terminal abaxial — Yellow-Green Group (146B); terminal adaxial — Green Group (139A). No anthocyanin on upper or lower surfaces of leaves or on leaf veins.

*Vein color of mature leaves*.—Adaxial side — Yellow-Green Group (145A); abaxial side — Yellow-Green Group (145A).

*Color of young leaves*.—Base abaxial — Yellow-Green Group (146C); base adaxial — Yellow-Green Group (146A); midpoint abaxial — Yellow-Green Group (146D); midpoint adaxial — Yellow-Green Group (146B); terminal abaxial — Yellow-Green Group (146D); terminal adaxial — Yellow-Green Group (146B).

Petioles: Petiole length is 10.7 cm and diameter is 3.1 mm.

Color on young leaves: Yellow-Green Group (146C).

Color of mature petioles: Red-Purple Group (60B).

*Petiole anthocyanin*.—Present on the adaxial surface of petiole where it meets the major leaf vein.

*Sinus of mature leaf*.—Is 2.94 cm deep and 2.35 cm at widest point.

*Mature leaves*.—Have sparse pubescence on the abaxial side that is prostrate and light on midrib, main veins and secondary veins. The adaxial side lacks pubescence.

*Young leaves*.—Have light sparse pubescence on midrib, main veins and secondary vein the abaxial side and light pubescence on veins of the adaxial side.

Tendrils: Found beginning on $4^{th}$ node, not opposite, but sometimes Intermittent.

*Length*.—10.8 cm.

*Texture*.—Smooth and usually forked and curled on distal end.

*Color of mature tendril*.—Yellow-Green Group 148B.

Buds:

*Average number of buds on a current, single-season cane*.—32.7.

*Dormant bud* (*compound bud or eye*).—Width 7.1 mm; shape triangular.

*Color*.—Greyed-Orange Group (165A).

*Texture*.—Smooth with some rough area.

Disease resistance: Moderately resistant to powdery mildew, and downy mildew; susceptible to black rot. Other disease or pest susceptibilities not known.

Flowers:

*Sex*.—Hermaphrodite.

*Date of bloom*.—May 10 (first), May 19 (full); May 24 (last).

*Flowers per cluster*.—110.

*Inflorescence length*.—10.6 cm.

*Inflorescence diameter*.—4.5 cm.

*Individual flower length*.—4.2 mm.

*Individual flower diameter*.—8.7 mm.

*Flower longevity on the plant*.—Short.

*Fragrance*.—Moderate smell, but not sweet.

*Stamens*.—Number: 5 to 6 and erect. Color: Yellow-Green Group (147C).

*Pistil*.—Number: 1. Length: 0.7 mm. Color: Yellow-Green Group (147C).

*Pollen*.—Color: Yellow Group (6D), normal and fertile.

*Petal*.—Cap of 6 used petals in tubular shape. Color Yellow-Green Group (147C).

*Sepal*.—None.

Fruit:

*Maturity*.—Early midseason; average first ripe dates July 15.

*Berry*.—Shape — Round. Skin Color — Greyed-Purple Group (183D). Bloom co1or — Grey Group (201B). Flesh color — Translucent, but tinted Yellow-Green Group (145A). Size — Diameter at equator: 1.7 cm. Diameter at base: 1.4 cm. Diameter at apex: 1.3 cm. Length: 1.8 cm. Weight: 3.12 g; uniform in size. Texture — Soft texture, typical of most *V. labrusca* cultivars, slipskin texture, indicating the skin separates from the pulp easily contributing to a non-crisp texture. Berry tenacity — High. Skin thickness — Medium. Seeds — Seedless with 1 small seed trace per berry. Brush length — 8.1 mm. Flavor — distinct *V. labrusca*-like flavor. Soluble solids — 22.0%.

*Juice*.—Berries are juicy. pH — 4.1. Titratable acidity — 1.2 g/L tartaric acid. Soluble solids — 22%.

*Storage*.—Berries are not recommended for storage or shipping due to the soft texture and are not recommended for storage except for homeowners for consumption soon after harvest.

*Cluster*.—Weight — 76.4-159.0 g, mean=107.9 gr. Length — 11.2 cm. Width — 5.1 cm. Berries per cluster — 32-66, mean=46. Cluster per vine — 40. Clusters per shoot — usually two. Peduncle length — 1.5 cm. Pedicle Length — 0.7 cm. Diameter — 0.13 cm. Color — Yellow-Green Group (146C).

*Use*.—Fresh consumption as a table grape is the primary use; home garden planting is suggested. No processing evaluations done.

THE CULTIVAR

The most distinctive features of the cultivar are its seedless, pink berries of distinct *V. labrusca*-like flavor, small compact clusters, distinctly lobed leaves, medium vigor, and healthy plant.

We claim:

1. A new and distinct cultivar of grape plant named 'A-1710' substantially as illustrated and described.

* * * * *